US012796903B2

(12) United States Patent
Eilat-Bloch et al.

(10) Patent No.: US 12,796,903 B2
(45) Date of Patent: Nov. 17, 2026

(54) SYSTEMS AND METHODS FOR REMOTE DENTAL MONITORING

(71) Applicant: GET-GRIN INC., Airmont, NY (US)

(72) Inventors: Yarden Eilat-Bloch, Haifa (IL); Pamela Sharon Oren-Artzi, Airmont, NY (US); Alon Luis Lipnik, Tel Aviv (IL); Adam Benjamin Schulhof, New City, NY (US); Carmi Raz, Gizo (IL)

(73) Assignee: Get-Grin Inc., Airmont, NY (US)

( * ) Notice: Subject to any disclaimer, the term of this patent is extended or adjusted under 35 U.S.C. 154(b) by 66 days.

(21) Appl. No.: 18/424,290

(22) Filed: Jan. 26, 2024

(65) Prior Publication Data

US 2024/0164631 A1 May 23, 2024

Related U.S. Application Data

(63) Continuation of application No. PCT/US2022/038736, filed on Jul. 28, 2022.

(Continued)

(51) Int. Cl.

*G03B 17/56* (2021.01)
*A61B 1/00* (2006.01)

(Continued)

(52) U.S. Cl.

CPC ............ *A61B 1/24* (2013.01); *A61B 1/00057* (2013.01); *A61B 1/00105* (2013.01);

(Continued)

(58) Field of Classification Search

CPC ... A61B 1/24; A61B 1/00057; A61B 1/00105; A61B 1/00121; A61B 1/0014; A61B 1/00165; A61B 1/046; A61B 1/053; A61B 1/0638; A61B 2560/0406; A61B 1/04; A61B 1/32; A61B 5/0013; A61B 5/0088; A61B 5/6898; A61C 9/0053

See application file for complete search history.

(56) References Cited

U.S. PATENT DOCUMENTS 770,368 A 9/1904 Heath
3,971,954 A 7/1976 Kleinberg et al.

(Continued)

FOREIGN PATENT DOCUMENTS

DE 202015102709 U1 8/2015
EP 1252858 A2 10/2002

(Continued)

OTHER PUBLICATIONS

PCT/US2021/019722 International Search Report and Written Opinion dated May 6, 2021.

(Continued)

*Primary Examiner* — Howard D Brown, Jr.

(74) *Attorney, Agent, or Firm* — Wolf, Greenfield & Sacks, P.C.

(57) ABSTRACT

The present disclosure provides an intraoral adapter comprising: an elongated housing comprising a viewing channel between a proximal portion and a distal portion of the elongated housing, wherein the viewing channel is configured to define a field of view of an intraoral region of a subject's mouth; and a connector configured to interchangeably accept and hold one or more external modules.

20 Claims, 4 Drawing Sheets

Related U.S. Application Data

(60) Provisional application No. 63/227,107, filed on Jul. 29, 2021.

(51) Int. Cl.
*A61B 1/04* (2006.01)
*A61B 1/05* (2006.01)
*A61B 1/06* (2006.01)
*A61B 1/24* (2006.01)
*G03B 23/08* (2006.01)

(52) U.S. Cl.
CPC ........ *A61B 1/00121* (2013.01); *A61B 1/0014* (2013.01); *A61B 1/00165* (2013.01); *A61B 1/046* (2022.02); *A61B 1/053* (2013.01); *A61B 1/0638* (2013.01); *A61B 2560/0406* (2013.01)

(56) References Cited

U.S. PATENT DOCUMENTS 4,664,628 A 5/1987 Totaro
4,889,490 A 12/1989 Jenkinson
5,338,198 A 8/1994 Wu et al.
6,151,172 A 11/2000 Ferraro
6,947,038 B1 9/2005 Anh et al.
7,077,647 B2 7/2006 Choi et al.
7,184,150 B2 2/2007 Quadling et al.
7,570,984 B2 8/2009 Katsuda et al.
7,625,335 B2 12/2009 Deichmann et al.
7,912,257 B2 3/2011 Paley et al.
7,912,673 B2 3/2011 Hebert et al.
8,562,338 B2 10/2013 Kitching et al.
8,998,609 B2 4/2015 Prakash et al.
9,014,440 B2 4/2015 Arumugam et al.
9,152,767 B2 10/2015 Mah
9,168,113 B2 10/2015 Wu et al.
9,324,190 B2 4/2016 Bell et al.
9,329,675 B2 5/2016 Ojelund et al.
9,439,568 B2 9/2016 Atiya et al.
D774,193 S 12/2016 Makmel et al.
9,510,757 B2 12/2016 Kopelman et al.
9,770,217 B2 9/2017 Sandholm et al.
9,788,917 B2 10/2017 Mah
9,808,148 B2 11/2017 Miller et al.
D806,248 S 12/2017 Makmel et al.
9,939,714 B1 4/2018 Matthews
9,987,108 B2 6/2018 Levin
10,032,271 B2 7/2018 Somasundaram et al.
D827,137 S 8/2018 Miller
10,108,269 B2 10/2018 Sabina et al.
10,123,706 B2 11/2018 Elbaz et al.
10,136,972 B2 11/2018 Sabina et al.
10,206,759 B2 2/2019 Salah et al.
10,242,443 B2 3/2019 Hsieh et al.
10,342,645 B2 7/2019 Salah et al.
10,357,342 B2 7/2019 Falkel
10,410,430 B2 9/2019 Somasundaram et al.
10,417,774 B2 9/2019 Salah et al.
10,463,451 B2 11/2019 Janzadeh et al.
10,467,815 B2 11/2019 Marom et al.
10,485,638 B2 11/2019 Salah et al.
10,492,893 B2 12/2019 Van Der Poel et al.
10,504,386 B2 12/2019 Levin et al.
10,588,501 B2 3/2020 Salah et al.
10,588,723 B2 3/2020 Falkel
10,595,966 B2 3/2020 Carrier, Jr. et al.
10,636,522 B2 4/2020 Katzman et al.
10,660,728 B2 5/2020 Maraj et al.
10,685,259 B2 6/2020 Salah et al.
10,736,715 B2 8/2020 Salah et al.
10,755,409 B2 8/2020 Salah et al.
10,779,718 B2 9/2020 Meyer et al.
10,779,909 B2 9/2020 Salah et al.
10,799,321 B2 10/2020 Salah et al.
10,803,146 B2 10/2020 Cosse
10,842,592 B2 11/2020 Salah et al.
10,849,723 B1 12/2020 Yancey et al.
D910,850 S 2/2021 Hansen et al.
10,925,698 B2 2/2021 Falkel
10,932,885 B2 3/2021 Carrier, Jr. et al.
10,966,667 B2 4/2021 Salah et al.
11,013,578 B2 5/2021 Salah
11,049,248 B2 6/2021 Salah et al.
D925,739 S 7/2021 Shalev et al.
11,083,551 B2 8/2021 Yancey et al.
11,107,218 B2 8/2021 Salah et al.
11,109,945 B2 9/2021 Salah et al.
11,191,617 B2 12/2021 Carrier, Jr. et al.
11,246,688 B2 2/2022 Salah et al.
11,270,523 B2 3/2022 Long et al.
11,291,532 B2 4/2022 Azernikov et al.
11,392,210 B2 7/2022 Sabina et al.
D962,437 S 8/2022 Oren-Artzi et al.
D971,407 S 11/2022 Liu et al.
D973,887 S 12/2022 Rohde, II et al.
11,638,636 B2 5/2023 Oren-Artzi et al.
D988,514 S 6/2023 Oren-Artzi et al.
11,957,528 B2 4/2024 Oren-Artzi et al.
12,102,465 B2 * 10/2024 Park .................... A61B 5/0088
12,144,492 B2 11/2024 Chambers et al.
12,349,871 B2 7/2025 Eilat-Bloch et al.
2002/0003620 A1 1/2002 Jung et al.
2002/0196438 A1 12/2002 Kerschbaumer et al.
2003/0148243 A1 8/2003 Kerschbaumer et al.
2004/0252303 A1 12/2004 Giorgianni et al.
2006/0001739 A1 1/2006 Babayoff
2006/0029903 A1 2/2006 Kobayashi
2006/0040230 A1 2/2006 Blanding et al.
2008/0172386 A1 7/2008 Ammar et al.
2008/0309924 A1 12/2008 Jung et al.
2009/0076321 A1 3/2009 Suyama et al.
2009/0167848 A1 7/2009 Eren et al.
2010/0311005 A1 12/2010 Liang
2011/0221878 A1 9/2011 Kitaoka et al.
2013/0096539 A1 4/2013 Wood et al.
2013/0209954 A1 8/2013 Prakash et al.
2013/0244197 A1 9/2013 Tjioe et al.
2013/0300919 A1 11/2013 Fletcher et al.
2014/0072189 A1 3/2014 Jena et al.
2014/0142390 A1 5/2014 Bromwich
2014/0232342 A1 8/2014 Turner
2015/0029309 A1 1/2015 Michaeli et al.
2015/0118638 A1 4/2015 Cowburn
2016/0374784 A1 12/2016 Joshi
2017/0027432 A1 2/2017 Wachs
2017/0258420 A1 9/2017 Inglese et al.
2017/0303857 A1 10/2017 Perkins et al.
2018/0125610 A1 5/2018 Carrier, Jr. et al.
2018/0160887 A1 6/2018 Hefez et al.
2018/0174367 A1 6/2018 Marom et al.
2018/0185125 A1 7/2018 Salah et al.
2018/0192964 A1 7/2018 Stalder et al.
2018/0228359 A1 8/2018 Meyer et al.
2018/0263730 A1 9/2018 Sirovskiy et al.
2018/0284580 A1 * 10/2018 Matthews .......... A61B 1/00034
2018/0296080 A1 10/2018 Glinec et al.
2018/0303331 A1 10/2018 Salah et al.
2018/0303579 A1 10/2018 Salah et al.
2018/0303580 A1 * 10/2018 Salah ................ A61B 1/00148
2018/0344430 A1 12/2018 Salah et al.
2019/0026598 A1 1/2019 Salah et al.
2019/0026599 A1 1/2019 Salah et al.
2019/0125493 A1 5/2019 Salah et al.
2019/0133717 A1 5/2019 Salah et al.
2019/0167115 A1 * 6/2019 Dorodvand .......... A61B 5/0088
2019/0200903 A1 7/2019 Watson
2019/0269485 A1 9/2019 Elbaz et al.
2019/0289283 A1 9/2019 Fisker et al.
2019/0307531 A1 10/2019 Wu et al.
2019/0313963 A1 10/2019 Hillen
2019/0328489 A1 10/2019 Capron-Richard et al.
2020/0297205 A1 9/2020 Hill et al.
2020/0334813 A1 10/2020 Salah et al.
2020/0404243 A1 12/2020 Saphier et al.

(56) References Cited

U.S. PATENT DOCUMENTS

| | | | |
|---|---|---|---|
| 2020/0405447 A1 | 12/2020 | Salah et al. | |
| 2021/0007834 A1 | 1/2021 | Salah et al. | |
| 2021/0045858 A1 | 2/2021 | Salah et al. | |
| 2021/0052138 A1 | 2/2021 | Bevis et al. | |
| 2021/0068923 A1 | 3/2021 | Carrier, Jr. et al. | |
| 2021/0106229 A1 | 4/2021 | Van Der Poel et al. | |
| 2021/0145550 A1 | 5/2021 | Salah et al. | |
| 2021/0158614 A1 | 5/2021 | Katzman et al. | |
| 2021/0161365 A1 | 6/2021 | Kim et al. | |
| 2021/0161621 A1 | 6/2021 | Salah et al. | |
| 2021/0186658 A1 | 6/2021 | Salah et al. | |
| 2021/0192724 A1 | 6/2021 | Salah et al. | |
| 2021/0244502 A1 | 8/2021 | Farkash et al. | |
| 2021/0259807 A1 | 8/2021 | Salah et al. | |
| 2021/0282634 A1 | 9/2021 | Oren-Artzi et al. | |
| 2021/0361387 A1 | 11/2021 | Salah et al. | |
| 2021/0366119 A1 | 11/2021 | Salah et al. | |
| 2021/0390687 A1 | 12/2021 | Salah et al. | |
| 2022/0087519 A1 | 3/2022 | Foged et al. | |
| 2022/0133383 A1 | 5/2022 | Chu et al. | |
| 2022/0338727 A1 | 10/2022 | Chambers et al. | |
| 2023/0346531 A1 | 11/2023 | Oren-Artzi et al. | |
| 2024/0126153 A1 | 4/2024 | Pellissard et al. | |
| 2024/0298891 A1 | 9/2024 | Eilat-Bloch et al. | |
| 2024/0298892 A1 | 9/2024 | Pellissard et al. | |
| 2024/0315546 A1 | 9/2024 | Eilat-Bloch et al. | |
| 2024/0341584 A1 | 10/2024 | Raz | |
| 2026/0007498 A1* | 1/2026 | Fain | A61C 9/0053 |

FOREIGN PATENT DOCUMENTS

| | | | |
|---|---|---|---|
| GB | 2587382 | A | 3/2021 |
| JP | 2007151782 | A | 6/2007 |
| JP | 4576325 | B2 | 11/2010 |
| JP | 2017031794 | A | 2/2017 |
| JP | 2018134418 | A | 8/2018 |
| KR | 101583547 | B1 | 1/2016 |
| TW | M503883 | U | 7/2015 |
| WO | WO-2011109630 | A2 | 9/2011 |
| WO | WO-2012038474 | A1 | 3/2012 |
| WO | WO-2015040917 | A1 | 3/2015 |
| WO | WO-2015082300 | A1 | 6/2015 |
| WO | WO-2016066651 | A1 | 5/2016 |
| WO | WO-2016185463 | A1 | 11/2016 |
| WO | WO-2018080413 | A2 | 5/2018 |
| WO | WO-2019149700 | A1 | 8/2019 |
| WO | WO-2019215129 | A1 | 11/2019 |
| WO | WO-2019224055 | A1 | 11/2019 |
| WO | WO-2020011863 | A1 | 1/2020 |
| WO | WO-2020011864 | A1 | 1/2020 |
| WO | WO-2020089248 | A1 | 5/2020 |
| WO | WO-2020185733 | A1 | 9/2020 |
| WO | WO-2021058930 | A1 | 4/2021 |
| WO | WO-2021161933 | A1 | 8/2021 |
| WO | WO-2021173867 | A1 | 9/2021 |
| WO | WO-2021236616 | A1 | 11/2021 |
| WO | WO-2023278354 | A1 | 1/2023 |
| WO | WO-2023009763 | A1 | 2/2023 |
| WO | WO-2023009764 | A1 | 2/2023 |
| WO | WO-2023009859 | A2 | 2/2023 |
| WO | WO-2023022953 | A1 | 2/2023 |
| WO | WO-2023096981 | A1 | 6/2023 |
| WO | WO-2023102121 | A1 | 6/2023 |
| WO | WO-2023133297 | A2 | 7/2023 |
| WO | WO-2023133297 | A3 | 9/2023 |
| WO | WO-2023205449 | A1 | 10/2023 |

OTHER PUBLICATIONS

PCT/US2022/038736 International Search Report and Written Opinion dated Nov. 1, 2022.

PCT/US2022/038736 Published Application dated Jan. 18, 2024.

PCT/US2022/050881 International Search Report and Written Opinion dated May 3, 2023.

PCT/US2022/051542 International Search Report and Written Opinion dated Apr. 14, 2023.

PCT/US2023/010355 International Search Report and Written Opinion dated Jul. 5, 2023.

PCT/US2023/019450 International Search Report and Written Opinion dated Jul. 18, 2023.

Co-pending U.S. Appl. No. 18/184,944, inventors Oren-Artzi; Pamela Sharon et al., filed Mar. 16, 2023.

Co-pending U.S. Appl. No. 18/424,290, inventor Eilat-Bloch; Yarden, filed Jan. 26, 2024.

Co-pending U.S. Appl. No. 18/603,067, inventors Oren-Artzi; Pamela Sharon et al., filed Mar. 12, 2024.

Co-pending U.S. Appl. No. 18/922,170, inventors Yarden; Eilat-Bloch et al., filed Oct. 21, 2024.

Co-pending U.S. Appl. No. 18/926,946, inventors Oren-Artzi; Pamela Sharon et al., filed Oct. 25, 2024.

Co-pending U.S. Appl. No. 29/731,805, inventors oren-artzi; Pamela Sharon et al., filed Apr. 17, 2020.

Co-pending U.S. Appl. No. 29/917,847, inventors Oren-Artzi; Pamela et al., filed Nov. 22, 2023.

Co-pending Design U.S. Appl. No. 29/734,658, inventors Oren-Artzi; Pamela Sharon et al., filed May 14, 2020.

Co-pending Design U.S. Appl. No. 29/889,942, inventors oren-artzi; Pamela Sharon et al., filed Apr. 18, 2023.

EP21760077.4 Extended European Search Report dated Feb. 21, 2024.

Maninis et al. Convolutional Oriented Boundaries: From Image Segmentation to High-Level Tasks, in IEEE Transactions on Pattern Analysis and Machine Intelligence, vol. 40, No. 4, pp. 819-833, (Apr. 28, 2017). Retrieved at URL: https://arxiv.org/pdf/1701.04658.

PCT/US2021/032932 International Search Report and Written Opinion dated Sep. 9, 2021.

PCT/US2022/035176 International Search Report and Written Opinion dated Sep. 15, 2022.

PCT/US2022/040265 International Search Report and Written Opinion dated Nov. 3, 2022.

U.S. Appl. No. 17/336,997 Office Action dated Sep. 9, 2021.

U.S. Appl. No. 62/417,985, inventors Carrier; Maurice et al., filed Nov. 4, 2016.

U.S. Appl. No. 17/336,997 Notice of Allowance dated Feb. 13, 2023.

U.S. Appl. No. 17/336,997 Office Action dated Apr. 12, 2022.

U.S. Appl. No. 17/336,997 Office Action dated Dec. 3, 2021.

U.S. Appl. No. 17/336,997 Office Action dated Sep. 2, 2022.

U.S. Appl. No. 18/349,878 Notice of Allowance dated Feb. 8, 2024.

U.S. Appl. No. 18/349,878 Office Action dated Sep. 26, 2023.

U.S. Appl. No. 29/734,658 Office Action dated Oct. 21, 2021.

U.S. Appl. No. 29/758,330 Notice of Allowance dated Apr. 28, 2022.

U.S. Appl. No. 29/758,330 Office Action dated Jan. 10, 2022.

U.S. Appl. No. 29/865,561 Notice of Allowance dated Feb. 23, 2023.

Co-pending U.S. Appl. No. 19/222,699, inventors Oren-Artzi; Pamela Sharon et al., filed May 29, 2025.

Co-pending U.S. Appl. No. 19/226,888, inventors Eilat-Bloch; Yarden et al., filed Jun. 3, 2025.

DENTALMONITORING. ScanBox pro tutorial for patient with aligners—english. YouTube (2021) https://www.youtube.com/watch?v=hIREJhQJL_s&t=29s.

EP22850340.5 Extended European Search Report dated May 13, 2025.

EP22902182.9 Extended European Search Report dated Sep. 16, 2025.

U.S. Appl. No. 18/922,170 Notice of Allowance dated Apr. 3, 2025.

U.S. Serial No. 18/922, 170 Office Action dated Jan. 2, 2025.

* cited by examiner

SYSTEMS AND METHODS FOR REMOTE DENTAL MONITORING

CROSS-REFERENCE TO RELATED APPLICATIONS

The present application is a continuation of International Patent Application PCT/US2022/038736 filed Jul. 28, 2022, which claims the benefit of U.S. Provisional Application Ser. No. 63/227,107 filed Jul. 29, 2021, each of which is incorporated by reference herein in its entirety.

TECHNICAL FIELD

The present invention, in at least some embodiments, relates to a method and a system for dental imaging, and more specifically a method and system for adapter for dental imaging using a mobile device.

BACKGROUND

Dental professionals and orthodontists may treat and monitor a patient's dental condition based on in-person visits. Treatment and monitoring of a patient's dental condition may require a patient to schedule multiple in-person visits to a dentist or orthodontist. The quality of treatment and the accuracy of monitoring may vary depending on how often and how consistently a patient sees a dentist or orthodontist. In some cases, suboptimal treatment outcomes may result if a patient is unable or unwilling to schedule regular visits to a dentist or orthodontist.

SUMMARY

Recognized herein is a need for remote dental monitoring solutions to allow dental patients to receive high quality dental care, without requiring a dental professional to be physically present with the patient. Some dental professionals and orthodontists may use conventional teledentistry solutions to accommodate patients' needs and schedules. However, such conventional teledentistry solutions may provide inadequate levels of supervision. Further, such conventional teledentistry solutions may be limited by an inaccurate or insufficient monitoring of a patient's dental condition based on one or more photos taken by the patient, if the photos do not adequately capture various intraoral features.

The present disclosure provides systems and methods for intraoral imaging to enhance remote dental monitoring capabilities. The systems and methods disclosed herein may provide a convenient solution and user experience for dental patients to capture one or more intraoral images using a mobile device such as a smartphone. The systems and methods disclosed herein may allow patients to achieve a wide enough occlusion view for improved self-scans of a full dental arch, and may be more appealing to patients than a conventional cheek retractor system. The systems and methods disclosed herein may enhance a patient's ability to assess or evaluate their dental condition based on one or more full arch self-scans, and may provide dentists and orthodontists with a detailed analysis of the patient's dental condition based on one or more full arch scans captured remotely by the patient.

In an aspect, the present disclosure provides an intraoral adapter comprising: an elongated housing comprising a viewing channel between a proximal portion and a distal portion of the elongated housing, wherein the viewing channel is configured to define a field of view of an intraoral region of a subject's mouth; and a connector configured to interchangeably accept and hold one or more external modules.

In some cases, the connector is located on a wall of the intraoral adapter. In some cases, the connector comprises a first magnet configured to couple to a second magnet located on a module of said one or more modules. In some cases, the connector is located on a corner of the intraoral adapter.

In some cases, the one or more modules comprises a camera element, an emitting source element, an optical element, an acoustic element, an antenna element, a calibration element, a ruler element, a holder element, a vent element, or a heating element. In some cases, the camera element is configured to capture infrared light, visible light, or ultraviolet light. In some cases, the emitting source element is configured to produce infrared light, visible light, ultraviolet light, temperature, one or more gases, sound, or radio frequency. In some cases, the optical element is configured to reflect, diffract, or refract light. In some cases, the optical element is selected from the group consisting of: a mirror, a lens, a prism, a prism sheet, an optical fiber, a polarizer, and a diffraction grating. In some cases, the calibration element is configured to calibrate between two points in a dental scan. In some cases, the calibration element is selected from the group consisting of: a calibration pattern, a colored target, a light reflection, an observation target, and a reference target.

In some cases, the one or more modules are configured to connect to a mobile device are configured to connect to a mobile device, and the mobile device is configured to provide energy or transfer data to the one or more modules via a wired or wireless connection. In some cases, the one or more modules are configured to be replaceable or interchangeable by a user. In some cases, the intraoral adapter further comprises a mounting mechanism on the distal portion of the elongated housing, wherein the mounting mechanism is configured to couple the intraoral adapter to a mobile device. In some cases, the mobile device comprises: (a) a camera configured to capture images or video, and (b) a storage element.

In another aspect, the present disclosure provides a method for intraoral imaging, comprising: (a) providing an intraoral adapter comprising a viewing channel configured to define a field of view of an intraoral region of a subject's mouth and a connector configured to interchangeably accept and hold one or more external modules, wherein a camera is configured to be coupled to the intraoral adapter; and (b) using the camera to capture intraoral images or videos through the viewing channel in conjunction with the operation of one or more external modules.

In some cases, the camera is located on a mobile device, and the mobile device comprises a storage element. In some cases, the one or more modules comprises a camera element, an emitting source element, an optical element, an acoustic element, an antenna element, a calibration element, a ruler element, a holder element, a vent element, or a heating element. In some cases, the camera element is configured to capture infrared light, visible light, or ultraviolet light. In some cases, the emitting source element is configured to produce infrared light, visible light, ultraviolet light, temperature, one or more gases, sound, or radio frequency. In some cases, the optical element is configured to reflect, diffract, or refract light. In some cases, the optical element is selected from the group consisting of: a mirror, a lens, a prism, a prism sheet, an optical fiber, a polarizer, and a diffraction grating.

In some cases, the intraoral images or videos are used to evaluate at least one tooth located in the intraoral region of the subject's mouth. In some cases, the status of an oral feature located in the intraoral region of the subject's mouth using the intraoral adapter of claim 1. In some cases, the status comprises enamel porosity, plaque deposition, tooth density, tooth location, tooth color, gum recession, color of gums, gum inflammation, tooth heat, tooth texture, tooth blood flow, or bacterial density.

In another aspect, the present disclosure provides an intraoral imaging system comprising: an intraoral adapter comprising a viewing channel between a proximal portion and a distal portion of the intraoral adapter, wherein the viewing channel is configured to define a field of view of an intraoral region of a subject's mouth; a connector configured to interchangeably accept and hold one or more external modules, wherein the intraoral adapter is configured to couple to a camera, and wherein the one or more modules are replaceable or removable to or from intraoral adapter by a user based at least partly on a desired module functionality.

In some cases, the connector is located on a wall of the intraoral adapter. In some cases, the connector comprises a first magnet configured to couple to a second magnet located on a module of said one or more modules. In some cases, the connector is located on a corner of the intraoral adapter. In some cases, the one or more modules comprises a camera element, an emitting source element, an optical element, an acoustic element, an antenna element, a calibration element, a ruler element, a holder element, a vent element, or a heating element. In some cases, the camera element is configured to capture infrared light, visible light, or ultraviolet light. In some cases, the emitting source element is configured to produce infrared light, visible light, ultraviolet light, temperature, one or more gases, sound, or radio frequency. In some cases, the optical element is configured to reflect, diffract, or refract light. In some cases, the optical element is selected from the group consisting of: a mirror, a lens, a prism, a prism sheet, an optical fiber, a polarizer, and a diffraction grating. In some cases, the calibration element is configured to calibrate between two points in a dental scan. In some cases, the calibration element is selected from the group consisting of: a calibration pattern, a colored target, a light reflection, an observation target, and a reference target.

In some cases, the one or more modules are configured to connect to a mobile device, wherein the mobile device is configured to provide energy or transfer data to the one or more modules via a wired or wireless connection. In some cases, the one or more modules are configured to be replaceable or interchangeable by a user. In some cases, the intraoral imaging system further comprises a mounting mechanism on the distal portion of the elongated housing, wherein the mounting mechanism is configured to couple the intraoral adapter to a mobile device. In some cases, the mobile device comprises (a) a camera configured to capture images or video, and (b) a storage element.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar structures, devices or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION

Figure 1C:
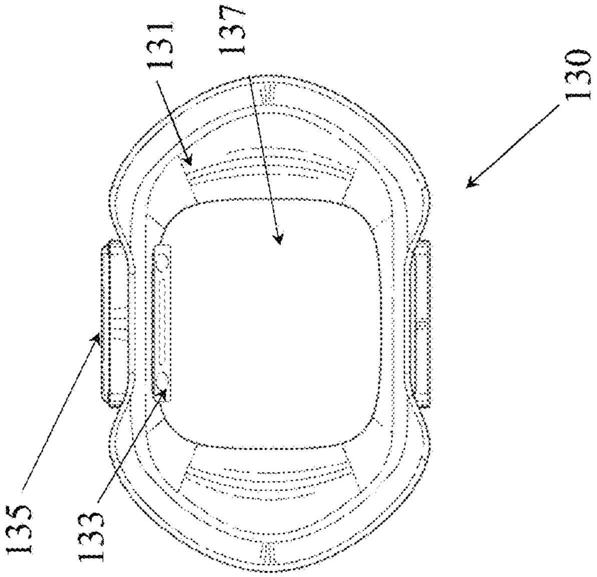
FIG. 1C schematically illustrates an example of an intraoral adapter comprising a connector for a module and an attached module, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "real-time," as used herein, generally refers to a simultaneous or substantially simultaneous occurrence of a first event or action with respect to an occurrence of a second event or action. A real-time action or event may be performed within a response time of less than one or more of the following: ten seconds, five seconds, one second, a tenth of a second, a hundredth of a second, a millisecond, or less relative to at least another event or action. A real-time action may be performed by one or more computer processors.

The term “intraoral adapter,” as used herein, generally refers to an object or device that can at least partly be set on the intraoral region of the mouth.

The term “dental scan,” as used herein, generally refers to a digital representation of the interior part of the mouth, usually the dental scan is an image or a video of at least part of an arch and including at least part of a teeth.

The terms “UV, visible light, IR”, as used herein, generally refers to sections in the electromagnetic spectrum. UV refers to ultraviolet light with wavelength in the range of 100 to 400 nm. Visible refers to light with a wavelength in the range of 100 to 700 nm (the part of the electromagnetic spectrum a human can see). IR refers to infrared light with a wavelength above 700 nm.

Whenever the term “at least,” “greater than,” or “greater than or equal to” precedes the first numerical value in a series of two or more numerical values, the term “at least,” “greater than” or “greater than or equal to” applies to each of the numerical values in that series of numerical values. For example, greater than or equal to 1, 2, or 3 is equivalent to greater than or equal to 1, greater than or equal to 2, or greater than or equal to 3.

Whenever the term “no more than,” “less than,” or “less than or equal to” precedes the first numerical value in a series of two or more numerical values, the term “no more than,” “less than,” or “less than or equal to” applies to each of the numerical values in that series of numerical values. For example, less than or equal to 3, 2, or 1 is equivalent to less than or equal to 3, less than or equal to 2, or less than or equal to 1.

The terms “a,” “an,” and “the,” as used herein, generally refer to singular and plural references unless the context clearly dictates otherwise.

The term “connector,” as used herein, refers to an element or location on an element that is used to couple two or more discrete components. A connector can be a physical connector that mechanically attaches two or more components together. A connector can be a magnetic location that is configured to attach a discrete component. A connector can use any mechanism to couple two or more discrete components. In some cases, a connector is configured to accept and hold another component. A connector may releasably couple two or more components.

Overview

In an aspect, the present disclosure provides an Intraoral adapter for dental scan, comprising a connector for a module; a module; an elongated housing comprising a viewing channel between a proximal portion and a distal portion of the elongated housing; wherein the connector enables the operation of the module in the viewing channel.

In some embodiments, the connection place for a module is on the interior wall of the intraoral adapter.

In some embodiments, the connection place for a module comprises a magnet and the modules comprises magnet.

In some embodiment the connection place for a module comprises a dent, hook or a screw in, and the module comprise revers dent, opposite hook or screw respectively or any other why of temporary attached the module.

In some embodiments, the connection place for a module is on the interior corner of the intraoral adapter.

Figure 1B:
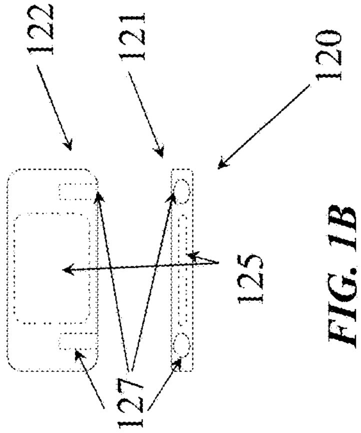
FIG. 1B schematically illustrates an example of an module, in accordance with some embodiments.
Figure 1A:
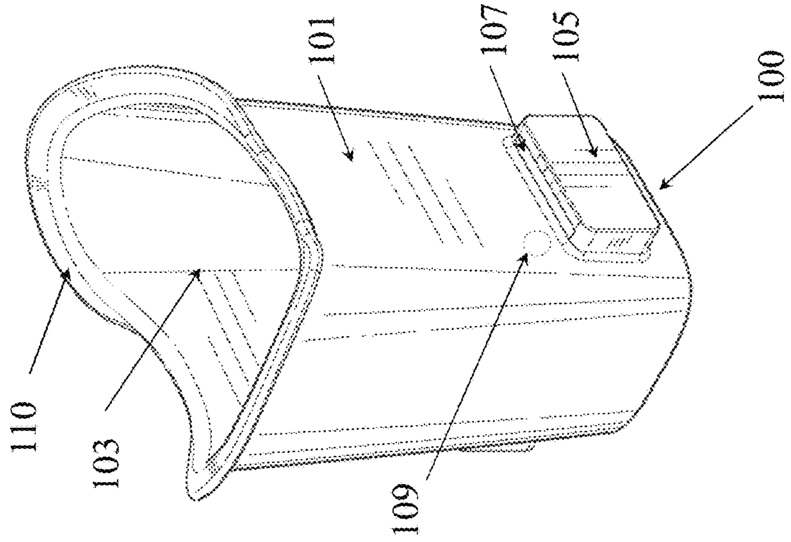
FIG. 1A schematically illustrates an example of an intraoral adapter comprising a connector for a module in accordance with some embodiments.

FIG. 1A schematically illustrates an example of an intraoral adapter 100 comprising a connector that can accept and hold a module 105 in accordance with some embodiments. The intraoral adapter 100 may comprise a viewing channel 103. The viewing channel 103 may comprise an elongated hollow region that extends from a distal end to the proximal end of the intraoral adapter 100. The viewing channel can be configured to permit one or more cameras of a mobile device to capture one or more intraoral images or intraoral videos through a length of the intraoral adapter.

The viewing channel 103 of the intraoral adapter may be configured to define a field of view of an intraoral region of a subject’s mouth. The field of view may be sized and/or shaped to permit one or more cameras of the mobile device to capture one or more images of one or more intraoral regions in a subject’s mouth. In some cases, the one or more images may comprise one or more intraoral images showing a portion of a subject’s mouth. In some cases, the one or more images may comprise one or more intraoral images showing a full dental arch of the subject.

The field of view may have a width that is at least about 1 inch, 2 inches, 3 inches, 4 inches, 5 inches, or more. The field of view may have a height that is at least about 1 inch, 2 inches, 3 inches, 4 inches, 5 inches, or more. The dimensions of the field of view may be adjusted or may vary depending on the anatomical characteristics of the subject or patient.

The intraoral adapter 100 can have a connector that can accept and hold a module 105. In some cases, the module is attached to the interior of the viewing channel 103. The connector may comprise a magnet 107 that enables the attachment of the module 105 to the intraoral adapter 100. The intraoral adapter 100 can have an open hole 109, which may allow for one or more cable connections from the module 105 to an external mobile device.

In some embodiments, the intraoral adapter 100 can comprise a flange 110. The flange may be configured to be inserted into an intraoral region of the subject’s mouth such that the flange is located between a lip portion and a gum portion of the subject’s mouth. The intraoral adapter may be suspended from the subject’s mouth when the flange 110 is positioned between the gum portion and the tooth portion of the subject’s mouth. The gum portion and the tooth portion may be in contact with a first side of the flange 110 and a second side of the flange 110 to support a weight of the intraoral adapter when the intraoral adapter is suspended from the subject’s mouth. The flange 110 may be sized and shaped to permit the subject to move the intraoral adapter and/or to adjust a position or an orientation of the intraoral adapter relative to one or more intraoral regions in the subject’s mouth. Adjusting the position or the orientation of the intraoral adapter relative to one or more intraoral regions in the subject’s mouth may also adjust a position or an orientation of the camera of the mobile device relative to the one or more intraoral regions in the subject’s mouth. Adjusting a position or an orientation of the camera of the mobile device relative to the one or more intraoral regions in the subject’s mouth may further adjust a relative position and/or a relative orientation of an optical axis of the camera relative to the one or more intraoral regions in the subject’s mouth. The flange 110 may remain between the gum portion and the tooth portion of the subject’s mouth while the subject moves the intraoral adapter around in the subject’s mouth. The flange 110 may be sized and shaped to permit the subject to capture one or more intraoral images of a full dental arch of the subject (or a portion thereof). In any of the embodiments described herein, the flange 140 of the intraoral adapter may be configured to be positioned outside the field of view defined by the viewing channel of the intraoral adapter. As described above, the field of view may be configured to provide a view of an intraoral region of the subject’s mouth. The flange 140 may be configured to extend radially outwards from a perimeter of the opening 160 such that the flange 140 is positioned outside the field of view 180 of the intraoral region of the subject's mouth. The flange may extend partially or continuously around a peripheral portion or perimeter of the opening. The flange may extend outwards from the peripheral portion or the perimeter of the opening.

In some cases, the flange may comprise a concave curvature that is configured to conform to a shape or a structure of a gum portion of the subject's mouth. The concave curvature may comprise one or more curved portions configured to conform to a curvature of one or more portions of the subject's gums. The one or more curved portions may have a radius of curvature ranging from about 0.1 inches to about 10 inches. In some embodiments, the radius of curvature may be less than or equal to about 0.1 inches. In other embodiments, the radius of curvature may be greater than or equal to about 10 inches.

The flange may be configured to extend from the body of the intraoral adapter at an angle. The angle may be at least about 5 degrees, 10 degrees, 15 degrees, 20 degrees, 25 degrees, 30 degrees, 35 degrees, 40 degrees, 45 degrees, 50 degrees, 60 degrees, 70 degrees, 80 degrees, 90 degrees, 100 degrees, 110 degrees, 120 degrees, or more.

In some cases, the flange may have a thickness that ranges from about 1 millimeter to about 10 millimeters. In some cases, the flange may have a thickness that is greater than about 10 millimeters. In some cases, the flange may extend outwards from a body of the intraoral adapter by at least about 1 millimeter to about 10 millimeters. In some cases, the flange may extend outwards from a body of the intraoral adapter by more than about 10 millimeters.

FIG. 1B schematically illustrates an example of a module 120, in accordance with some embodiments. Module 120 is presented in a top view perspective 122 and a front view 121. The exemplary module 120 may comprise a magnet 125 and a light source 127. The module can be attached to the interior of the viewing channel 103 of the of FIG. 1A.

Figure 2B:
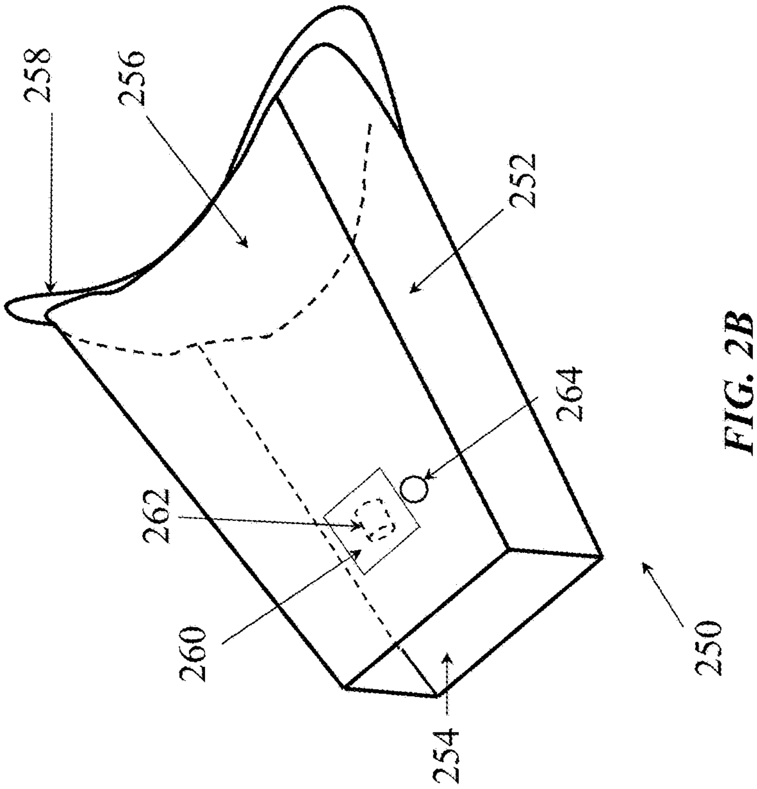
FIGS. 2A and 2B schematically illustrate an example of an intraoral adapter comprising a connector for a module and an attached module, in accordance with some embodiments.
Figure 2A:
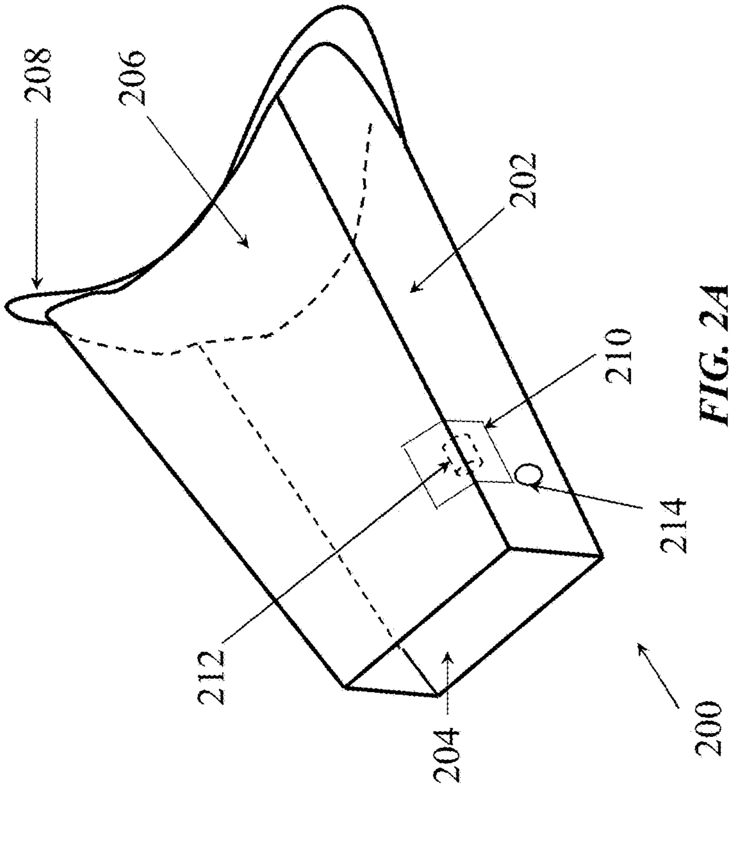

FIG. 1C schematically illustrates 130 an example of an intraoral adapter 130 comprising a connector for a module and an attached exemplary module 133, in accordance with some embodiments. The intraoral adapter 131 may comprise a connector 135 and a viewing channel 137. In some cases, the module 133 is located on the inside of the viewing channel 137. The module 133 may attach to the connector 135. The module 133 may attach to the connector 135 through magnetic attraction. In some cases, the module 133 comprises a magnet, and the connector 135 comprises a magnet. The module 133 may be configured to be FIG. 2A schematically illustrate an example of an intraoral adapter 200 comprising a connector 210 that can accept and hold a module 212 and an attached module 212. In some cases, as illustrated in FIG. 2A, the module is connected to the corner of the interior of the viewing channel 206. The intraoral adapter 200 may comprise a viewing channel 206 between a distal opening 204 and a proximal opening 206. In some cases, the intraoral adapter 200 has a connector 210 that can accept and hold a module 212. The module may be freely removed and attached at the discretion of a user. The intraoral adapter 200 may have an open hole 214, which may allow for one or more cable connections from the module 212 to an external mobile device. In some embodiments, the flange 208 is part of the intraoral adapter 202. FIG. 2B schematically illustrate an example of an intraoral adapter 250 comprising a connector 260 for a module 262 and an attached module. In some cases, the module is connected to an interior wall of a viewing channel 256. The intraoral adapter 250 may comprise a viewing channel between a distal opening 254 and proximal opening 256. The intraoral adapter may have a connector 260 for a module 262 that can accept and hold a module 262. The module may be freely removed and attached at the discretion of a user. The intraoral adapter 250 may have an open hole 264, which may allow for one or more cable connections from the module 212 to an external mobile device. In some cases, the intraoral adapter comprises a flange 258.

Module

In some embodiments, the module is selected from a group containing; camera element, emitting source element, optical element, acoustic element, antenna element, calibration element, ruler element, holder element, vent element, heating element.

In some embodiments, the camera element can capture IR, visible, or UV light. In some embodiments the camera element provides an additional camera in addition to the mobile device camera. In some cases, the additional camera can be used to capture additional angles or perspectives that the mobile device camera is not able to capture. In some embodiments the camera element has features that the mobile camera lacks.

An emitting source element may be used to emit any kind of radiation that can be used to distinguish one tooth from another. In some embodiments, the emitting source element produces at least one of IR Light, visible light, UV light, heat, gas, sound, or radio frequency. In some cases, an emitting element is used to receive feedback from the emitting source. For example, an emitting element may emit radiation into the mouth of a patient, and the antenna element can measure the radiation the feedback of radiation that leaves the patient.

The optical element can be configured to reflect, diffract, or refract light. In some embodiments, the optical element is a mirror, lens, Fresnel lens, prism, prism sheet, optical fiber, polarizer, or diffraction grating.

The acoustic element can be configured to detect or emit sound. The sound may be supersonic. In some cases, the acoustic element emits a sound into the mouth of a patient. The sound may reach the patient's mouth and reverberate back towards the intraoral adapter. A detection device may be used to detect the reverberated sound. Differences in the reverberated sound may be used to determine the status of a tooth. For example, a damaged or decayed tooth may have different acoustic different properties than a healthy tooth, so the reverberated sound may be different between a healthy and sick tooth. In another example, a fake tooth or a tooth with dental work (like a filling or a crown) may have different acoustic different properties than a real tooth, so the reverberated sound may be different between a fake and real tooth.

The calibration element can be configured to provide perspective between two points in a dental scan. In some embodiments, the calibration element is comprised of at least one of a calibration pattern, colored target, light reflection, observation target, or reference target.

The ruler element may be used to measure intraoral features in a patient's mouth. These measurements may be relative. In some embodiments, the ruler element is in the metric system or imperial system. In some embodiments, the ruler presents measurements in more than one dimension. In some embodiments, the ruler presents real distances. In some embodiments, the ruler presents distances that can be used to predict a location of a target intraoral tissue.

In some embodiment, the holder element can be used to hold a part of intraoral tissue. The holder may be used to hold a part of the intraoral tissue out of the way of a camera or viewing channel so the intraoral tissue does not interfere with dental imagine. In some cases, the holder holds the tongue, cheek, or gums of a patient.

In some embodiments, the vent element can be a fan used to vent air out of the intraoral adapter chamber. A vent may reduce humidity in the intraoral adapter chamber, which can impact the quality of a dental image or video due to fogging up a camera or providing obstructions in the viewing channel.

In some embodiments, the heating element is used to reduce the humidity in the intraoral adapter chamber. A heating element may reduce humidity in the intraoral adapter chamber, which can impact the quality of a dental image or video due to fogging up a camera or providing obstructions in the viewing channel.

In some embodiments, the module can connect to a mobile device mobile device configured to provide energy or transfer data to the module via a wired or wireless connection.

In some embodiments, the module is selected from a set of optional modules. In some cases, a user can add or remove a module from the intraoral adapter at will. The user can also add or remove a module from the intraoral adapter at the instruction of a dental professional. For example, a dental professional may advise a user to add a venting or heating element to the intraoral adapter because the user's images are blurry due to excess humidity in the adapter.

Mounting Mechanism

In some embodiments, the intraoral adapter, further comprising a mounting mechanism provided on the distal portion of the elongated housing, wherein the mounting mechanism is configured to couple the intraoral adapter to a mobile device.

In some embodiments, the mobile device comprises a camera, ability to capture images or/and video and a storage element.

In some cases, the intraoral adapter may further comprise a mounting mechanism. The mounting mechanism may be provided on the distal portion of the elongated housing. The mounting mechanism may be configured to couple the intraoral adapter to a mobile device comprising a camera. The mounting mechanism may be configured to couple the mobile device to the intraoral adapter such that a longitudinal axis of the viewing channel is substantially aligned with an optical axis of the camera of the mobile device. The longitudinal axis of the viewing channel may extend from the distal portion of the elongated housing to the proximal portion of the elongated housing. The longitudinal axis may coincide with a central axis of the intraoral adapter that extends from a center of a first opening of the elongated housing to a center of a second opening of the elongated housing. The first opening of the elongated housing may be located at a distal portion of the elongated housing, and the second opening of the elongated housing may be located at a proximal portion of the elongated housing. The optical axis of the camera may correspond to an imaging axis that extends from the lens of the camera to the one or more intraoral regions of the subject's mouth. The imaging axis may be substantially orthogonal to the lens of the camera.

The mounting mechanism of the intraoral adapter may be configured to mechanically engage with a mobile device or a casing of the mobile device. The mounting mechanism may comprise an elastic band, a clamp, a hook, a magnet, a bracket, or a holder. The mounting mechanism may be configured to provide the mobile device in a fixed position and/or a fixed orientation relative to the elongated housing, an opening of the elongated housing, or a structural component of the elongated housing or intraoral adapter.

Figure 3B:
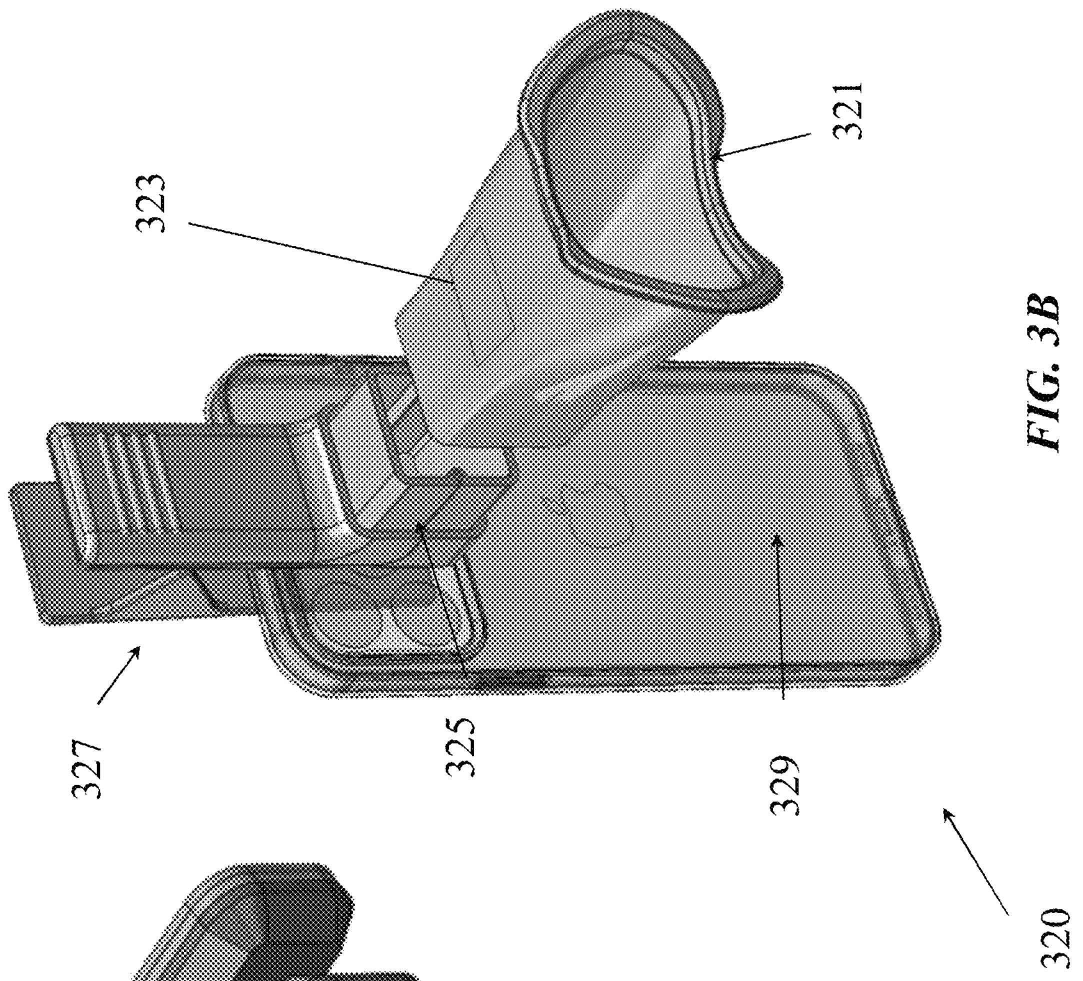
FIGS. 3A and 3B schematically illustrates an exemplary intraoral adapter comprising a connector for a module and exemplary mounting mechanism, in accordance with some embodiments.
Figure 3A:
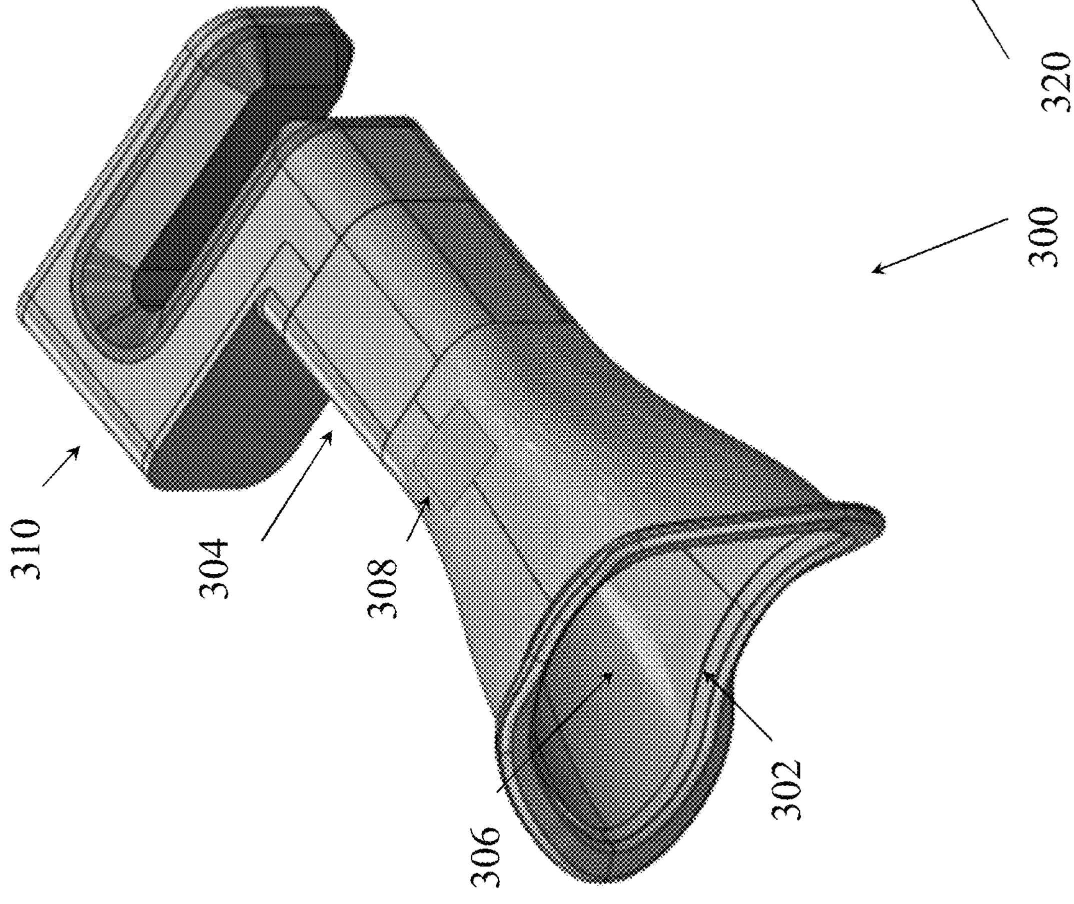

FIG. 3A illustrates an example of an intraoral adapter 300 comprising a connector for a module and exemplary mounting mechanism, in accordance with some embodiments. The intraoral adapter 300 may have a viewing channel 306 and a connector that can accept and hold a module 308. The module may be freely removed and attached at the discretion of a user. The intraoral adapter 300 may be attached to a mobile device mounting mechanism 310. The mounting mechanism 310 of the intraoral adapter 300 may be configured to mechanically engage with a mobile device or a casing of the mobile device.

FIG. 3B illustrates an example of an intraoral adapter 320 comprising a connector for a module and exemplary mounting mechanism, in accordance with some embodiments. The intraoral adapter 320 may have a connector that can accept and hold a module 323. The module may be freely removed or replaced at the discretion of a user. The intraoral adapter 320 may be attached to a mobile device mounting mechanism 327. The mounting mechanism 327 of the intraoral adapter 320 may be configured to mechanically engage via an attachment 325 with a mobile device 329 or a casing of the mobile device. The mounting mechanism 327 can be a clamp.

Dental Scan

The present disclosure provides a method to generate a dental scan using an intraoral adapter for a dental scan comprising: providing an intraoral adapter comprising a connector for a module and elongated housing comprising a viewing channel between a proximal portion and a distal portion of the elongated housing and a mounting mechanism provided on the distal portion of the elongated housing configured to couple the intraoral adapter to a mobile device; providing at least one module selected from a group of optional modules; providing a mobile device; connecting the module into the connection place in the intraoral adapter; mounting the intraoral adapter to the mobile device; and placing the intraoral adapter into user mouth.

Figure 4:
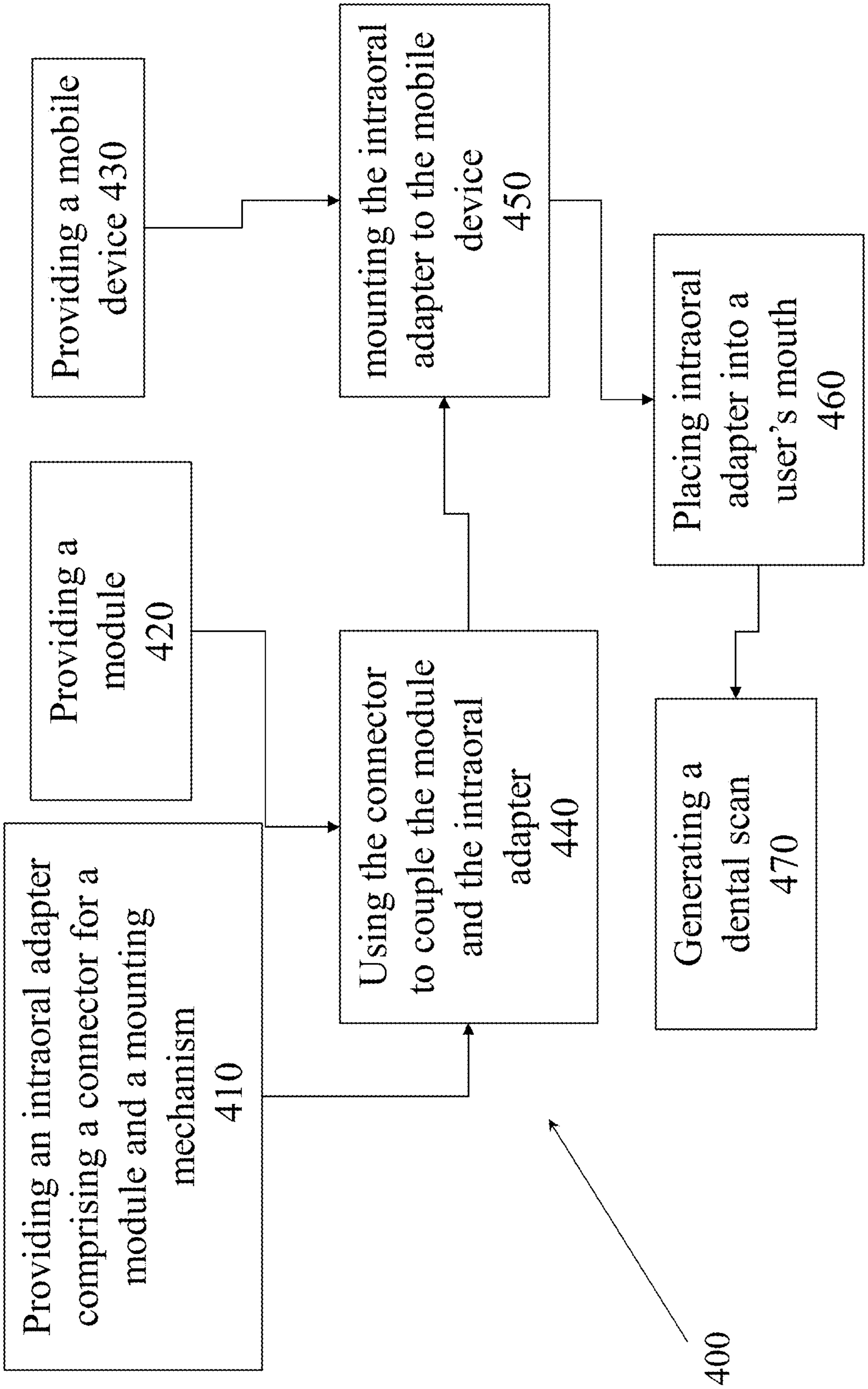
FIG. 4 schematically illustrates a method to use intraoral adapter comprising a connector, in accordance with some embodiments.

FIG. 4 schematically illustrates a method to generate a dental scan using an intraoral adapter for a dental scan 400, the method comprises providing an intraoral adapter comprising a connector for a module, an elongated housing comprising a viewing channel between a proximal portion and a distal portion of the elongated housing, and a mounting mechanism provided on the distal portion of the elongated housing configured to couple the intraoral adapter to a mobile device 410; providing at least one module selected from a group of optional modules 420; providing a mobile device 430; connecting the module into the connector of the intraoral adapter 440; mounting the intraoral adapter to the mobile device 450; placing the intraoral adapter into user mouth 460; and generating a dental scan 470.

In some embodiments, the mobile device comprises a camera, ability to capture images or/and video and storage element.

In some embodiments, the camera element can capture IR, visible, or UV light. In some embodiments the camera element provides an additional camera in addition to the mobile device camera. In some cases, the additional camera can be used to capture additional angles or perspectives that the mobile device camera is not able to capture. In some embodiments the camera element has features that the mobile camera lacks.

In another aspect, the present disclosure provides method for intraoral imaging, comprising: (a) providing an intraoral adapter comprising a viewing channel configured to define a field of view of an intraoral region of a subject's mouth and a connector configured to interchangeably accept and hold one or more external modules, wherein a camera is configured to be coupled to the intraoral adapter; and (b) using the camera to capture intraoral images or videos through the viewing channel in conjunction with the operation of the one or more external modules.

In some cases, the camera is located on a mobile device, and wherein the mobile device comprises a storage element.

In some cases, the one or more modules comprises a camera element, an emitting source element, an optical element, an acoustic element, an antenna element, a calibration element, a ruler element, a holder element, a vent element, or a heating element.

In some cases, the camera element is configured to capture infrared light, visible light, or ultraviolet light.

In some cases, the emitting source element is configured to produce infrared light, visible light, ultraviolet light, temperature, one or more gases, sound, or radio frequency.

In some cases, the optical element is configured to reflect, diffract, or refract light.

In some cases, the optical element is selected from the group consisting of: a mirror, a lens, a prism, a prism sheet, an optical fiber, a polarizer, and a diffraction grating.

In some cases, the intraoral images or videos are used to evaluate at least one tooth located in the intraoral region of the subject's mouth.

In some cases, the status of an oral feature located in the intraoral region of the subject's mouth using the intraoral adapter of claim 1.

In some cases, the status comprises enamel porosity, plaque deposition, tooth density, tooth location, tooth color, gum recession, color of gums, gum inflammation, tooth heat, tooth texture, tooth blood flow, or bacterial density.

In another aspect, the present disclosure provides an intraoral imaging system. The intraoral imaging system may comprise an intraoral adapter as described elsewhere herein. The intraoral adapter may be operably coupled to a mobile device having one or more cameras. The intraoral imaging system may further comprise an image processing unit configured to (i) process a plurality of intraoral images captured using the camera of the mobile device, and (ii) determine a dental condition of the subject based at least in part on the plurality of intraoral images.

In some cases, the image processing unit may be located onboard the mobile device. In other cases, the image processing unit may be located on one or more servers that are remote from the mobile device.

The image processing unit may be configured to process a plurality of intraoral images. The plurality of intraoral images may be captured using a camera of a mobile device. Processing the plurality of intraoral images may comprise comparing a first set of pixel values within an intraoral image to a second set of pixel values within the intraoral image. The pixel values may comprise a value corresponding to a color or a brightness of one or more pixels. In some cases, processing the plurality of intraoral images may comprise comparing one or more pixel values within an intraoral image to a set of reference pixel values within a reference image. The set of reference pixel values may be accessed through a database that is located remote from a mobile device of a user. In some cases, the set of reference pixel values may indicate a certain dental condition (e.g., a presence of plaque or a presence of cavities). In some cases, processing the plurality of intraoral images may comprise comparing a first intraoral image to a second intraoral image. Comparing a first intraoral image to a second intraoral image may comprise tracking a movement of one or more features that are visible within the first intraoral image and the second intraoral image. Comparing a first intraoral image to a second intraoral image may comprise tracking a change in a shape of a subject's dental arches between the first intraoral image and the second intraoral image. In some cases, comparing a first intraoral image to a second intraoral image may comprise tracking a change in one or more pixel values between the first intraoral image and the second intraoral image. In some cases, the first intraoral image and the second intraoral image may be obtained within a single scanning session. In some cases, the first intraoral image may be obtained during a first scanning session and the second intraoral image may be obtained during a second scanning session that is initiated after the first scanning session.

The image processing unit may be configured to determine a dental condition of the subject based at least in part on the plurality of intraoral images captured using the camera of the mobile device. The dental condition may comprise (i) a movement of one or more teeth of the subject, (ii) an accumulation of plaque on the one or more teeth of the subject, (iii) a change in a color or a structure of the one or more teeth of the subject, (iv) a change in a color or a structure of a tissue adjacent to the one or more teeth of the subject, and/or (v) a presence or lack of presence of one or more cavities. In some cases, the plurality of intraoral images may be used to (i) predict a movement of one or more teeth of the subject, (ii) identify enamel wear patterns, (iii) create or modify a dental treatment plan, or (iv) generate or update an electronic medical record associated with a dental condition of the subject.

The image processing unit may be configured to determine a dental condition of the subject based at least in part on the three-dimensional model. The dental condition may comprise (i) a movement of one or more teeth of the subject, (ii) an accumulation of plaque on the one or more teeth of the subject, (iii) a change in a color or a structure of the one or more teeth of the subject, (iv) a change in a color or a structure of a tissue adjacent to the one or more teeth of the subject, and/or (v) a presence or lack of presence of one or more cavities. In some cases, the three-dimensional model may be used to (i) predict a movement of one or more teeth of the subject, (ii) identify enamel wear patterns, (iii) create or modify a dental treatment plan, or (iv) generate or update an electronic medical record associated with a dental condition of the subject.

As used herein, remote monitoring may refer to monitoring a dental anatomy or a dental condition of a patient that is performed at one or more locations remote from the patient. For example, a dentist or a medical specialist may monitor the dental anatomy or dental condition in a first location that is different than a second location where the patient is located. The first location and the second location may be separated by a distance spanning at least 1 meter, 1 kilometer, 10 kilometers, 100 kilometers, 1000 kilometers, or more. The remote monitoring may be performed by assessing a dental anatomy or a dental condition of the subject using one or more intraoral images captured by the subject when the patient is located remotely from the dentist or a dental office. In some cases, the remote monitoring may be performed in real-time such that a dentist is able to assess the dental anatomy or the dental condition when a subject uses a mobile device to acquire one or more intraoral images of one or more intraoral regions in the patient's mouth. The remote monitoring may be performed using equipment, hardware, and/or software that is not physically located at a dental office.

Intraoral Adapter—Elements

The intraoral adapter may comprise an elongated housing comprising a viewing channel between a proximal portion and a distal portion of the elongated housing.

The module may comprise a first material. The first material may comprise a soft, compliant material. The first material may comprise a rubber material, a silicone material, a polymeric material, a thermoplastic elastomer, and/or a synthetic rubber material such as styrene-butadiene rubber, ethylene propylene diene monomer rubber, isoprene, chloroprene, polychloroprene, neoprene, or isobutylene. The intraoral adapter may comprise a second material. The second material may comprise a plastic material. The plastic material may comprise polyethylene terephthalate (PETE or PET), high-density polyethylene (HDPE), polyvinyl chloride (PVC), low-density polyethylene (LDPE), polypropylene (PP), polycarbonate, polylactide, acrylic, acrylonitrile butadiene, styrene, fiberglass, nylon, and/or any combination thereof. In some cases, the second material may comprise a metallic material. The metallic material may comprise steels such as carbon steels and/or stainless steels, pure metals such as copper and/or aluminum, or metal alloys such as bronze and/or brass. In some cases, the second material may comprise a combination of plastic materials and metallic materials. In some cases, the second material may be different than the first material. In other cases, the second material may be the same as the first material.

In some cases, the first material and/or the second material may comprise polyvinyl chloride, polyvinylidene chloride, low density polyethylene, linear low density polyethylene, polyisobutene, poly[ethylene-vinylacetate] copolymer, and/or thermoplastics such as polyaryletherketone (PAEK), polyetheretherketone (PEEK), polyetherketoneketone (PEKK), polyetherketone (PEK), carbon-PEEK composites, PEEK-BaSO4 polymeric rubbers, polyethylene terephthalate (PET), silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, and/or rigid polymers including polyphenylene, wpolyamide, polyimide, polyetherimide, polyethylene, or epoxy. In some cases, the first material and/or the second material may comprise acrylobutadiene styrene (ABS), polypropylene (PP), polystyrene (PS), polycarbonate (PC), polysulfone (PS), polyphenyl sulfone (PPSU), polymethyl methacrylate (acrylic) (PMMA), polyethylene (PE), ultra high molecular weight polyethylene (UHMWPE), lower density polyethylene (LPDE), polyamide (PA), liquid crystal polymer (LCP), polyaryl amide (PARA), polyphenyl sulfide (PPS), polyether etherketone (PEEK), polyvinyl chloride (PVC), polyethylene terephthalate (PET), polytetraflouroethylene (PTFE), polyaryletherketone (PAEK), polyphenyl sulfone (PPSU), and/or a combination thereof.

In some cases, the module and/or the intraoral adapter may comprise a material that is manufacturable using stereolithography. In such cases, the material may comprise one or more photosensitive resins or thermoset polymers. The one or more photosensitive resins or thermoset polymers may be selectively cured layer-by-layer when exposed to a light source. In some cases, the light source may comprise an ultraviolet (UV) light or laser beam.

In some cases, the module and/or the intraoral adapter may comprise a biocompatible material. A biocompatible material may comprise a material that is compatible for use with biological materials. A biocompatible material may comprise a material that does not produce allergic reactions and/or toxic or injurious effects on the subject when placed in the subject's mouth. The biocompatible material may not elicit any undesirable local or systemic biological or physiological effects when placed in the subject's mouth. In some examples, the biocompatible material may comprise one or more polymeric materials including, but not limited to, thermosets, elastomers, and/or other polymeric materials that may be created by polymerizing monomers and/or cross-linking oligomers. In other examples, the biocompatible material may comprise materials such as cellophane, vinyl, acetate, polyethylene acrylic, butyl rubber, ethylene-vinyl acetate, natural rubber, a nitrile, silicone rubber, a styrene block copolymer, and/or a vinyl ether. Optionally, in any of the embodiments disclosed herein, the biocompatible material may comprise one or more antimicrobial and/or antiseptic materials, for example sodium bicarbonate; hydrogen peroxide; benzalkonium chloride; chlorohexidine; hexachlorophene; iodine compounds; and/or any combinations thereof.

Shapes

In some cases, a cross-section of the viewing channel may be in a circular or elliptical shape. In some cases, a cross-section of the viewing channel may be in a shape that comprises at least three or more sides. In some cases, the cross-section of the viewing channel may be in a hexagonal shape. In some cases, the cross-section of the viewing channel may be in a regular shape that comprises two or more sides with a same length. In other cases, the cross-section of the viewing channel may be in an irregular shape that comprises two or more sides with different lengths.

In some cases, the field of view may have a circular or elliptical shape. In some cases, the field of view may have a shape that comprises at least three or more sides. In some cases, the field of view may have a hexagonal shape. In some cases, the field of view may have a regular shape that comprises two or more sides with a same length. In some cases, the field of view may have an irregular shape that comprises two or more sides with different lengths. The field of view may be sized and shaped to improve capture of one or more intraoral images or intraoral videos of one or more molar regions of the subject's mouth. The field of view may be sized and/or shaped to reduce or minimize an amount of movement and/or adjustment needed by the subject to align an optical axis of the camera of the mobile device with the one or more molar regions.

In some cases, a cross-sectional shape of the viewing channel may comprise an irregular or amorphous shape. In some cases, a shape of the flange may comprise an irregular or amorphous shape. In some cases, a shape of the field of view may comprise an irregular or amorphous shape. An irregular shape may comprise a shape with a plurality of sides having one or more different lengths. An amorphous shape may comprise a shape that does not correspond to a circle, an ellipse, or a polygon.

Computer Systems

In an aspect, the present disclosure provides computer systems that are programmed or otherwise configured to implement methods of the disclosure. The computer system may be configured to, for example, process dental video scan or captured using the camera of the mobile device, and update the 3D model. The computer system may be configured to, for example, process orientation or motion sensors data using the orientation or motion sensors of the mobile device, and determine at least one of the dental scan properties during the dental scan. The computer system may be configured to activate a feedback element to generate output. The computer system can be an electronic device of a user or a computer system that is remotely located with respect to the electronic device. The electronic device can be a mobile electronic device. The computer system can be a smartphone.

The computer system may include a central processing unit (CPU, also "processor" and "computer processor" herein), which can be a single core or multi core processor, or a plurality of processors for parallel processing. The computer system also includes memory or memory location (e.g., random-access memory, read-only memory, flash memory), electronic storage unit (e.g., hard disk, Solid State drive or equivalent storage unit), communication interface (e.g., network adapter) for communicating with one or more other systems, and peripheral devices, such as cache, other memory, data storage and/or electronic display adapters. The memory, storage unit, interface and peripheral devices are in communication with the CPU through a communication bus (solid lines), such as a motherboard. The storage unit can be a data storage unit (or data repository) for storing data. The computer system can be operatively coupled to a computer network ("network") with the aid of the communication interface. The network can be the Internet, an internet and/or extranet, or an intranet and/or extranet that is in communication with the Internet. The network in some cases is a telecommunication and/or data network. The network can include one or more computer servers, which can enable distributed computing, such as cloud computing. The network, in some cases with the aid of the computer system, can implement a peer-to-peer network, which may enable devices coupled to the computer system to behave as a client or a server.

The CPU can execute a sequence of machine-readable instructions, which can be embodied in a program or software. The instructions may be stored in a memory location, such as the memory. The instructions can be directed to the CPU, which can subsequently program or otherwise configure the CPU to implement methods of the present disclosure. Examples of operations performed by the CPU can include fetch, decode, execute, and writeback.

The CPU can be part of a circuit, such as an integrated circuit. One or more other components of the system can be included in the circuit. In some cases, the circuit is an application specific integrated circuit (ASIC).

The storage unit can store files, such as drivers, libraries and saved programs. The storage unit can store user data, e.g., user preferences and user programs. The computer system in some cases can include one or more additional data storage units that are located external to the computer system (e.g., on a remote server that is in communication with the computer system through an intranet or the Internet).

The computer system can communicate with one or more remote computer systems through the network. For instance, the computer system can communicate with a remote computer system of a user (e.g., a subject, a dental patient, or a dentist). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system via the network.

Methods as described herein can be implemented by way of machine (e.g., computer processor) executable code stored on an electronic storage location of the computer system, such as, for example, on the memory or electronic storage unit. The machine executable or machine readable code can be provided in the form of software. During use, the code can be executed by the processor. In some cases, the code can be retrieved from the storage unit and stored on the memory for ready access by the processor. In some situations, the electronic storage unit can be precluded, and machine-executable instructions are stored on memory.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a storage unit. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system can include or be in communication with an electronic display that comprises a user interface (UI) for providing, for example, a portal for a subject or a dental patient to view one or more intraoral images or videos captured using a mobile device of the subject or the dental patient. In some cases, the electronic display may be the feedback element providing the generated output, for example displaying message or shape or light in accordance to some embodiments. In some cases, the user interface (UI) may be the feedback element providing the generated output, for example generating sound or voice message in accordance to some embodiments. The portal may be provided through an application programming interface (API). A user or entity can also interact with various elements in the portal via the UI. Examples of UI's include, without limitation, a graphical user interface (GUI) and web-based user interface.

The computer system can include or be in communication with a Camera for providing, for example, ability to capture videos or images of the subject or a dental patient. And for example, retrieve at least one dental scan date (such as optical object distance) that can be used to analyzed and compered to at least one dental scan properties Methods and systems of the present disclosure can be implemented by way of one or more algorithms. An algorithm can be implemented by way of software upon execution by the central processing unit. The algorithm can, for example, implement a method for dental scan. The method may comprise processing videos or images captured using the camera of the mobile device or processing dental scan data sensed by at least one sensor that can be used to analyze and compare to at least one dental scan properties and executed to generate output.

While embodiments have been shown and described herein, it will be obvious to those skilled in the art that such embodiments are provided by way of example only. It is not intended that the systems and methods described herein be limited by the specific examples provided within the specification. While the systems and methods described herein has been described with reference to the aforementioned specification, the descriptions and illustrations of the embodiments herein are not meant to be construed in a limiting sense.

Numerous variations, changes, and substitutions will now occur to those skilled in the art without departing from the systems and methods described herein. Furthermore, it shall be understood that all aspects of the systems and methods described herein are not limited to the specific depictions, configurations or relative proportions set forth herein which depend upon a variety of conditions and variables. It should be understood that various alternatives to the embodiments described herein may be employed in practicing the systems and methods described herein. It is therefore contemplated that the systems and methods described herein shall also cover any such alternatives, modifications, variations or equivalents. It is intended that the following claims define the scope of the systems and methods described herein and that methods and structures within the scope of these claims and their equivalents be covered thereby.

What is claimed is:

1. An intraoral adapter comprising:

an elongated housing comprising a viewing channel between a proximal portion and a distal portion of the elongated housing, wherein the viewing channel is configured to define a field of view of an intraoral region of a subject's mouth;

a mounting mechanism on the distal portion of the elongated housing, wherein the mounting mechanism is configured to couple the intraoral adapter to a mobile device; and a connector connected to the elongated housing, wherein the connector is configured to interchangeably accept and hold one or more external modules, wherein the one or more external modules are distinct from the mobile device and are held by the connector within the viewing channel, wherein the viewing channel and the modules allow direct field of view of at least part of the intraoral region of the subject's mouth.

2. The intraoral adapter of claim 1, wherein the connector is located on a wall of the intraoral adapter.

3. The intraoral adapter of claim 1, wherein the connector comprises a first magnet configured to couple to a second magnet located on a module of the one or more modules.

4. The intraoral adapter of claim 1, wherein the connector is located on a corner of the intraoral adapter.

5. The intraoral adapter of claim 1, wherein the one or more modules comprises a camera element, an emitting source element, an optical element, an acoustic element, an antenna element, a calibration element, a ruler element, a holder element, a vent element, or a heating element.

6. The intraoral adapter of claim 5, wherein the camera element is configured to capture infrared light, visible light, or ultraviolet light.

7. The intraoral adapter of claim 5, wherein the emitting source element is configured to produce infrared light, visible light, ultraviolet light, temperature, one or more gases, sound, or radio frequency.

8. The intraoral adapter of claim 5, wherein the optical element is configured to reflect, diffract, or refract light.

9. The intraoral adapter of claim 5, wherein the optical element is selected from the group consisting of: a mirror, a lens, a prism, a prism sheet, an optical fiber, a polarizer, and a diffraction grating.

10. The intraoral adapter of claim 5, wherein the calibration element is configured to calibrate between two or more points in a dental scan.

11. The intraoral adapter of claim 5, wherein the calibration element is selected from the group consisting of: a calibration pattern, a colored target, a light reflection, an observation target, and a reference target.

12. The intraoral adapter of claim 1, wherein the one or more modules are configured to couple to a mobile device, wherein the mobile device is configured to provide energy or transfer data to the one or more modules via a wired or wireless connection.

13. The intraoral adapter of claim 1, wherein the one or more modules are configured to be replaceable or interchangeable by a user.

14. The intraoral adapter of claim 1, wherein the mobile device comprises:

(a) a camera configured to capture images or video, and (b) a storage element.

15. The intraoral adapter of claim 1, further comprising a flange configured to be inserted into the intraoral region of the subject's mouth such that the flange is located between a lip portion and a gum portion of the subject's mouth, wherein the intraoral adapter is suspended from the subject's mouth when the flange is positioned between the gum portion and a tooth portion of the subject's mouth.

16. The intraoral adapter of claim 15, wherein the flange comprises a concave curvature configured to conform to a shape of the gum portion of the subject's mouth.

17. The intraoral adapter of claim 1, wherein the mounting mechanism comprises an elastic band, a clamp, a hook, a magnet, a bracket, or a holder.

18. The intraoral adapter of claim 1, wherein the mounting mechanism is configured to couple the mobile device to the intraoral adapter such that a longitudinal axis of the viewing channel is substantially aligned with an optical axis of a camera of the mobile device.

19. The intraoral adapter of claim 5, wherein the acoustic element is configured to emit a sound into the subject's mouth and to detect the sound reverberated back toward the intraoral adapter to determine a status of a tooth.

20. The intraoral adapter of claim 5, wherein the vent element comprises a fan configured to vent air out of the intraoral adapter to reduce humidity within the intraoral adapter.

* * * * *